(12) United States Patent
Waters et al.

(10) Patent No.: US 8,835,688 B2
(45) Date of Patent: Sep. 16, 2014

(54) OPTIMIZED INTRODUCTION OF THE STARTING MATERIALS FOR A PROCESS FOR PREPARING AROMATIC AMINES BY HYDROGENATION OF NITROAROMATICS

(75) Inventors: Gerrit Waters, Karlsruhe (DE); Johannes Buettner, Ruhland (DE); Andreas Raichle, Ludwigshafen (DE); Markus Hiller, Maxdorf (DE); Peter Renze, Mannheim (DE); Michael Herrich, Jannowitz (DE); Helmut Rueger, Schipkau (DE); Burkhard Hantel, Schwepnitz (DE); Arndt Hofmann, Radebeul (DE); Ruediger Fritz, Bernsdorf (DE); Kathrin Richter, Dresden (DE); Holgar Braunsberg, Senftenberg (DE); Lothar Bruntsch, Grossthiemig (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/421,453

(22) Filed: Mar. 15, 2012

(65) Prior Publication Data

US 2012/0238779 A1     Sep. 20, 2012

Related U.S. Application Data

(60) Provisional application No. 61/453,147, filed on Mar. 16, 2011.

(51) Int. Cl.
 *C07C 209/00* (2006.01)
 *B01J 8/22* (2006.01)
 *C07C 209/36* (2006.01)

(52) U.S. Cl.
 CPC ........ *B01J 8/226* (2013.01); *B01J 2208/00141* (2013.01); *B01J 2208/0015* (2013.01); *C07C 209/36* (2013.01); *B01J 2208/00911* (2013.01); *B01J 2208/00902* (2013.01); *B01J 2208/00123* (2013.01); *B01J 8/228* (2013.01); *B01J 2208/00132* (2013.01)
 USPC ....................................... 564/420

(58) Field of Classification Search
 None
 See application file for complete search history.

(56) References Cited

U.S. PATENT DOCUMENTS

| 5,563,296 A | 10/1996 | Zarnack et al. |
| 6,350,911 B1 * | 2/2002 | Sander et al. ............... 564/305 |
| 2001/0027257 A1 | 10/2001 | Marion |
| 2005/0119505 A1 | 6/2005 | Zehner et al. |
| 2011/0284391 A1 | 11/2011 | Fritz et al. |
| 2011/0295039 A1 | 12/2011 | Raichle et al. |

FOREIGN PATENT DOCUMENTS

| DE | 198 44 901 C1 | 11/1999 |
| EP | 0 634 391 A1 | 1/1995 |
| EP | 1 161 297 B1 | 10/2003 |
| EP | 1 165 231 B1 | 10/2003 |
| JP | 2008-222623 | 9/2008 |
| WO | 98/55216 | 12/1998 |
| WO | 00/35852 | 6/2000 |
| WO | 03/068724 A1 | 8/2003 |
| WO | 2006/089906 A1 | 8/2006 |
| WO | WO 2011/144481 A1 | 11/2011 |
| WO | WO 2011/144594 A1 | 11/2011 |
| WO | WO 2012/076449 A1 | 6/2012 |
| WO | WO 2012/104254 A1 | 8/2012 |

OTHER PUBLICATIONS

U.S. Appl. No. 13/311,371, filed Dec. 5, 2011, Haase, et al.
U.S. Appl. No. 13/362,607, filed Jan. 31, 2012, Allardt, et al.
U.S. Appl. No. 13/759,466, filed Feb. 5, 2013, Raichle, et al.
European Search Report issued Jul. 12, 2011, in Patent Application No. 11158462.9 (With English Translation of Category of Cited Documents).
U.S. Appl. No. 14/147,805, filed Jan. 6, 2014, Bey, et al.
U.S. Appl. No. 14/147,823, filed Jan. 6, 2014, Bey, et al.

* cited by examiner

*Primary Examiner* — Clinton Brooks
(74) *Attorney, Agent, or Firm* — Oblon, Spivak, McClelland, Maier & Neustadt, L.L.P.

(57) ABSTRACT

The invention relates to a process for preparing aromatic amines by hydrogenation of corresponding nitroaromatics by means of hydrogen, and also an apparatus suitable for this purpose. In particular, the invention relates to a process for preparing toluenediamine (TDA) by hydrogenation of dinitrotoluene (DNT).

17 Claims, 3 Drawing Sheets

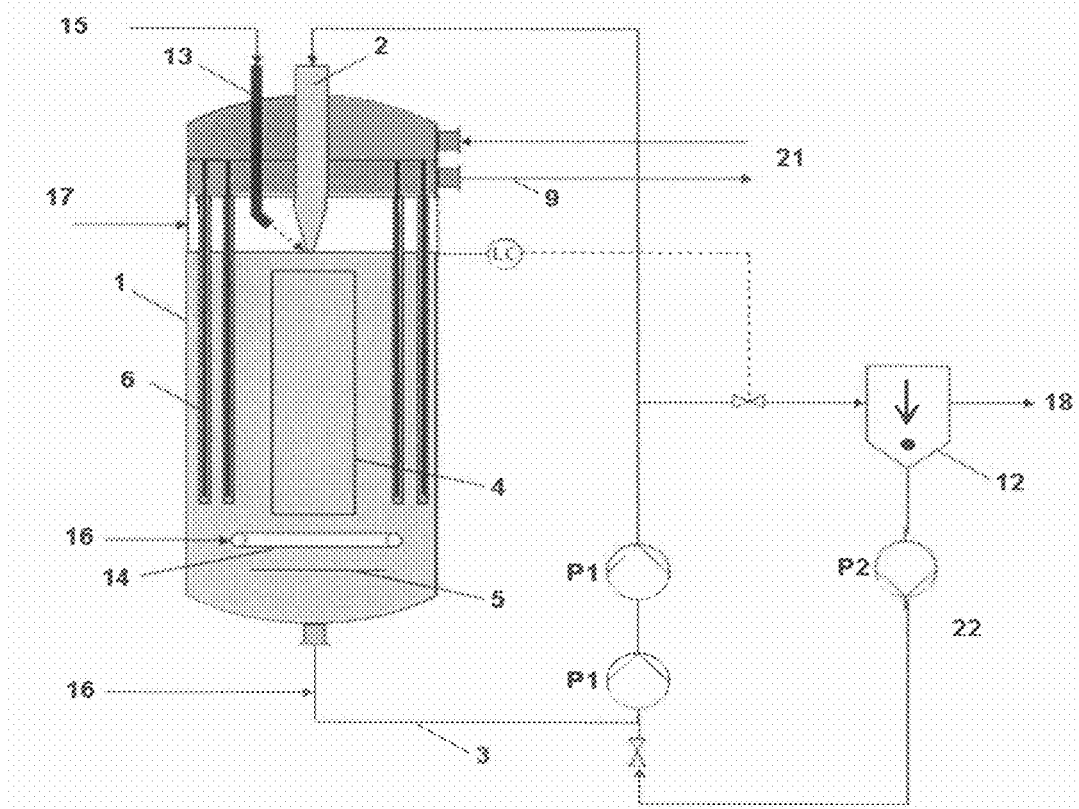

Figure 1A:
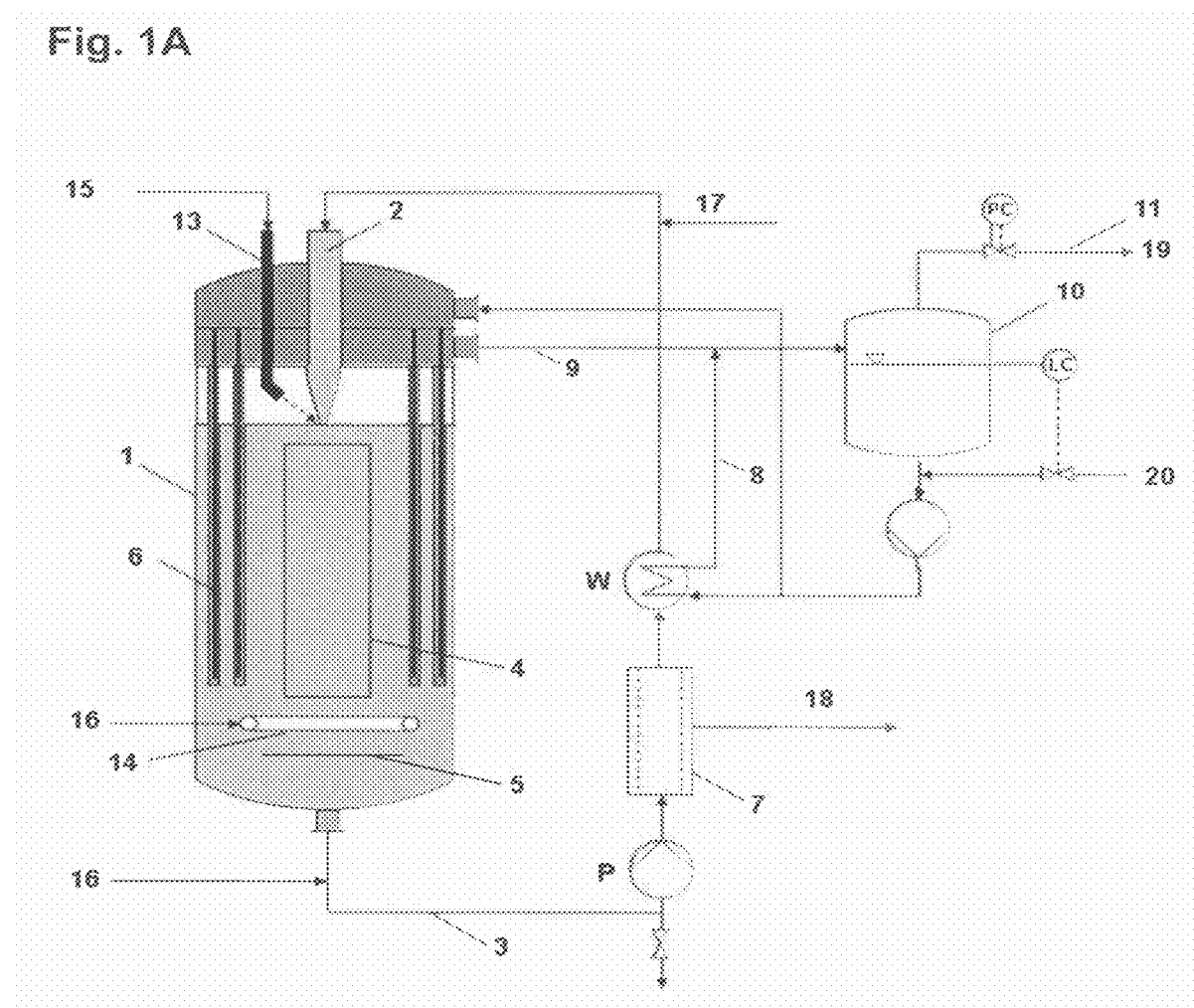

OPTIMIZED INTRODUCTION OF THE STARTING MATERIALS FOR A PROCESS FOR PREPARING AROMATIC AMINES BY HYDROGENATION OF NITROAROMATICS

The invention relates to a process for preparing aromatic amines by hydrogenation of corresponding nitroaromatics by means of hydrogen, and also an apparatus suitable for this purpose. In particular, the invention relates to a process for preparing toluenediamine (TDA) by hydrogenation of dinitrotoluene (DNT).

Toluenediamine is an aromatic amine which is frequently used in industry. It is processed further to form, in particular, tolylene diisocyanate which is predominantly used in polyurethane production. Toluenediamine is prepared by catalytic hydrogenation of dinitrotoluene.

In the preparation of toluenediamine from corresponding dinitrotoluenes, it is possible for a self-accelerating decomposition of dinitrotoluene to occur above a particular temperature and concentration, which represents a safety risk in processes carried out industrially. A further problem in the industrial preparation of toluenediamines from dinitrotoluenes is that, owing to the materials properties of the participating substances and also due to the presence of a suspended catalyst, local blocking of reactor elements can occur. A further problem in the industrial preparation of toluenediamines from dinitrotoluenes is that elevated DNT concentrations in the reaction mixture can damage the catalyst. To minimize the catalyst consumption, very rapid mixing in of the freshly introduced DNT while avoiding significant local overconcentrations is advantageous.

Processes for preparing corresponding toluenediamines by hydrogenation of dinitrotoluenes are already known from the prior art.

WO 98/55216 A1 discloses a shell-and-tube reactor for fast, strong exothermic reactions. In particular, this reactor is suitable for the liquid-phase hydrogenation of dinitrotoluene to the corresponding diamines. The problem of an excessively high concentration of dinitrotoluenes is not described in this document, since the focus of this document is on being able to remove the heat of reaction evolved in the strong exothermic reaction as efficiently as possible.

JP 2008/222623 discloses a method of stopping organic reactions, in particular the hydrogenation of aromatic nitro compounds to the corresponding aromatic amines, in a controlled manner. For this purpose, the addition of the respective dinitro compound and the catalyst is firstly interrupted. Only then is the addition of hydrogen interrupted. Thus, the method described in this document avoids the occurrence of a potentially hazardous high concentration of dinitrotolunes in the reactor.

US 2001/0027257 A1 discloses a process for the continuous hydrogenation of aromatic nitro compounds in the presence of a suitable catalyst. The concentration of the aromatic nitro compound should preferably be less than 1000 ppm, which according to this document is achieved by monitoring and controlling the addition of aromatic dinitro compounds.

WO 00/35852 A1 discloses a process for preparing amines by hydrogenation of nitro compounds, in which the hydrogenation is carried out in a vertical reactor whose length is greater than its diameter and has a downward-directed jet nozzle via which the starting materials and the reaction mixture are introduced arranged in the upper region of the reactor and also has an offtake which is located at any place in the reactor and via which the reaction mixture is circulated in an external circuit by means of a transport device back to the jet nozzle and also a flow reversal in the lower region of the reactor. This document does not disclose the problems of an excessively high concentration of dinitrotoluenes.

DE 198 44 901 C1 discloses a process for introducing liquid nitroaromatics having more than one nitro group into reactors for liquid-phase hydrogenation. For this purpose, the nitroaromatic to be reacted is circulated by pumping in one or more ring lines, with these ring lines running entirely or partly in the hydrogenation reactor and being provided in the interior of the reactor with outlets into the interior of the reactor.

WO 2006/089906 A1 discloses a process for preparing aromatic amines or aliphatic amino alcohols, in which the concentration of the nitrocompounds used or nitroso compounds formed has to be monitored in order to be able to rule out safety risks. The object of said document is achieved by online monitoring of the concentration of nitro and nitroso compounds in the reactor, for example by measuring the absorption of UV-VIS radiation in the reaction mixture.

WO 03/068724 A1 likewise discloses a process for preparing amines by hydrogenation of the corresponding nitro compounds. Furthermore, mention is made of the problem that the concentration of nitro compounds must not be too high in order to avoid a safety risk. The solution presented in this document is to inject a particular amount of hydrogen into the reaction mixture.

The as yet unpublished European patent application number EP 10162924.4 relates to a process for the continuous preparation of toluenediamine by liquid-phase hydrogenation of dinitrotoluene by means of hydrogen in the presence of a suspended, nickel-comprising catalyst in a reactor having a product separation unit located downstream of the reactor to give a product output from the reactor comprising a liquid phase comprising toluenediamine and dinitrotoluene, in which the nickel-comprising catalyst is suspended, where the concentration of dinitrotoluene in the liquid phase of the product output from the reactor in the region between the reactor and the downstream product separation unit is set to a value in the range from 1 to 200 ppm by weight, based on the total weight of the liquid phase of the product output from the reactor.

The processes of the prior art are in need of improvement in terms of avoidance of blockages due to starting materials, in particular nitroaromatics, for example dinitrotoluene compounds, catalysts and/or products, in particular the aromatic amines, preferably toluenediamine (TDA).

For the purposes of the present invention, blockages are formation of solid, insoluble deposits comprising organic and/or inorganic components within the one or more feed lines for the nitroaromatic. These deposits comprise, for example, starting material, product, polymeric compounds formed from the starting material and/or product, catalyst and/or possibly further substances present in the reaction solution.

As a result of blockages formed, there is the possibility of unnoticed formation of dead zones through which very little flow occurs and in which not only starting material, i.e. nitroaromatic, but also product, polymeric compounds formed from the starting material and/or product, catalyst and/or possibly further substances present in the reaction solution can be present. Above a temperature of about 260° C., a self-accelerating decomposition of nitroaromatic, for example pure dinitrotoluene (DNT), can occur. Contact of DNT with the product mixture can reduce this value down to below 100° C. and thus possibly below the reaction temperature. The simultaneous occurrence of a reduction in the decomposition temperature of the DNT as a result of contact with product and also longer residence times in dead zones results in a safety risk when carrying out the process.

Furthermore, blocking of particular reactor parts by the abovementioned compounds leads to the reactor having to be cleaned from time to time, which inevitably requires a shutdown of the preferably continuously operating reactor and thus a deterioration in the economics and yield of such a reactor.

It is therefore an object of the present invention to provide a process for preparing aromatic amines by hydrogenation of the corresponding nitroaromatics, by means of which formation of blockages composed of the starting materials used, the catalyst present and products formed being formed within the one or more feed lines for the nitroaromatic can be effectively avoided. These blockages should be kept low in order to keep the risk of explosion low. A further object is to provide a process of this type which can be carried out continuously over a long period of time without malfunctions on the reactor which can occur as a result of the abovementioned blockages occurring. It is also an object of the present invention to provide a process of this type in which very fast mixing of the nitroaromatic, preferably the dinitrotoluene, occurs and local overconcentrations which promote catalyst deactivation are avoided to the best possible extent.

These objects are achieved by the process of the invention for preparing aromatic amines by hydrogenation of nitroaromatics by means of hydrogen in the presence of a suspended catalyst in the liquid phase
in a reactor (1),
at one end of which, preferably the upper end, there is a driving jet nozzle (2) via which the reaction mixture taken off from the bottom region of the reactor is injected via an external loop (3) into this region of the reactor (1),
with introduction of the nitroaromatic at one end, preferably the upper end, of the reactor (1) and
introduction of hydrogen,
wherein
at the correct fill height of the reactor, no direct physical contact between the inlet for the nitroaromatic and the liquid phase, preferably comprising the desired aromatic amine, water and catalyst, can occur in the reactor and/or in the pumped circuit either in the operating state or on shutting down and
partial or complete blocking of the inlet for the nitroaromatic after improper contact between the inlet for the nitroaromatic and the liquid phase in the reactor can be detected by means of measuring instruments.

Many catalysts have been developed for the hydrogenation of nitroaromatics to aromatic amines, in particular of dinitrotoluene to toluenediamine, with improvement of the yield and selectivity in the reaction and the stability of the catalysts even at relatively high reaction temperatures having been predominant objectives in the development of new catalysts.

Catalysts which comprise one or more metals selected from the group consisting of platinum, palladium, rhodium, ruthenium and mixtures thereof and in addition one or more further metals selected from the group consisting of nickel, cobalt, iron, zinc and mixtures thereof as active composition applied to an inert support have been found to be particularly useful.

Catalysts comprising platinum and also nickel or catalysts comprising palladium, nickel and iron or catalysts comprising palladium, nickel and cobalt as active composition are especially advantageous.

Hydrogenation catalysts comprising platinum and nickel in the form of an alloy on a support having an atomic ratio of nickel to platinum in the alloy in the range from 30:70 to 70:30 are particularly advantageous.

Alloys of platinum and nickel having other atomic ratios can in principle also be used for the process of the invention, but they lead, especially when the hydrogenation is carried out at relatively high temperatures, to low yields of aromatic amine.

The atomic ratio of nickel to platinum, determined by means of EDXS (energy dispersive X-ray spectroscopy) is in particular in the range from 45:55 to 55:45.

The catalyst usually comprises finely crystalline metal particles of the Pt—Ni alloy having a size of about 1-15 nm distributed on, for example, carbon particles. Pt—Ni particle agglomerates or aggregates having a size of 1-2 µm and also isolated pure Ni or Pt particles can occur in places on the support. The electron diffraction lines of the metal particles are between those of Pt and Ni, which provides additional evidence of alloy formation. The metal particles are mostly polycrystalline and can be characterized by means of high-resolution TEM (FEG-TEM: field emission gun transmission electron microscopy).

As supports for the catalysts, it is possible to use the materials which are customary and known for this purpose. Preference is given to using activated carbon, carbon black, graphite or metal oxides, preferably hydrothermally stable metal oxides such as $ZrO_2$, $TiO_2$. In the case of graphite, HSAGs (high surface area graphites) having a surface area of from 50 to 300 $m^2/g$ are particularly preferred. Particular preference is given to physically or chemically activated activated carbon or carbon blacks such as acetylene black.

Further suitable catalysts comprise nickel either alone or together with at least one metal of transition groups I, V, VI and/or VIII of the Periodic Table as active component. The catalysts can be produced industrially by application of nickel and optionally at least one of the abovementioned additional metals to a suitable support or by coprecipitation. In this preferred embodiment of the invention, the catalyst has a nickel content in the range from 0.1 to 99% by weight, preferably from 1 to 90% by weight, particularly preferably from 25 to 85% by weight and very particularly preferably from 60 to 80% by weight, based on the total weight of the catalyst. Preference is given to using palladium, platinum, rhodium, iron, cobalt, zinc, chromium, vanadium, copper, silver or a mixture of two or more thereof as metals of transition groups I, II, V, VI and/or VIII of the Periodic Table. As support materials, preference is given to using activated carbon, carbon black, graphite or oxidic support components such as silicon dioxide, silicon carbide, kieselguhr, aluminum oxide, magnesium oxide, titanium dioxide, zirconium dioxide and/or hafnium dioxide or a mixture of two or more thereof, particularly preferably zirconium dioxide, $ZrO_2$, $HfO_2$ and/or $SiO_2$, $ZrO_2$ and/or $SiO_2$, $ZrO_2$, $HfO_2$. Suitable catalysts for this embodiment are described, for example, in the documents EP 1 161 297 A1 and EP 1 165 231 A1.

Nitroaromatics are used as starting material for the process of the invention. In a preferred embodiment of the process of the invention, mononitroaromatics or dinitroaromatics are used, and particular preference is given according to the invention to hydrogenating dinitroaromatics to the corresponding aromatic diamines.

Preferred mononitroaromatics are, for example, selected from the group consisting of nitrobenzene, nitrotoluene, for example 2-nitrotoluene, 3-nitrotoluene and/or 4-nitrotoluene, and mixtures thereof. According to the invention, nitrobenzene can be hydrogenated to aniline. Furthermore, nitrotoluene can be hydrogenated to the corresponding toluidines.

Preferred dinitroaromatics are, for example, selected from the group consisting of dinitrobenzene, for example 1,2-dinitrobenzene, 1,3-dinitrobenzene and/or 1,4-dinitrobenzene, dinitrotoluene and mixtures thereof. According to the invention, dinitrobenzene can be hydrogenated to diaminobenzene. Furthermore, dinitrotoluene can be hydrogenated to the corresponding toluenediamine isomers.

Preference is given according to the invention to using dinitrotoluene (DNT). Dinitrotoluene is known per se to those skilled in the art and can be present as various isomers, as shown below

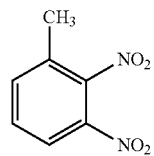
(Ia)

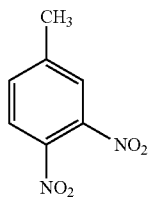
(IIa)

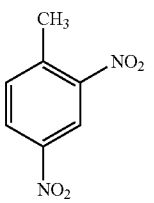
(IIIa)

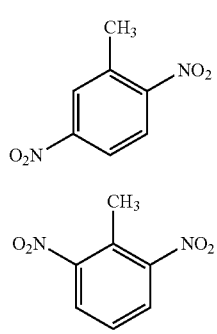
(IVa)
(Va)

According to the invention, it is possible to use a single isomer selected from among 2,3-dinitrotoluene (Ia), 3,4-dinitrotoluene (IIa), 2,4-dinitrotoluene (IIIa), 2,5-dinitrotoluene (IVa) and 2,6-dinitrotoluene (Va). However, it is also possible according to the invention and preferred to use a mixture comprising at least two of the isomers mentioned, for example a mixture comprising 2,4-dinitrotoluene (IIIa) and 2,6-dinitrotoluene (Va). In a preferred embodiment of the process of the invention, a mixture of dinitrotoluene isomers as is obtained in the double nitration of toluene is used.

In a preferred embodiment, the corresponding toluenediamines are obtained as product of the process of the invention after hydrogenation. The possible isomers are shown below.

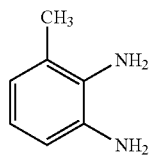
(Ib)

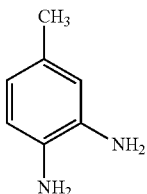
(IIb)

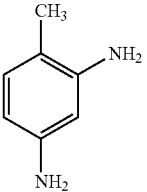
(IIIb)

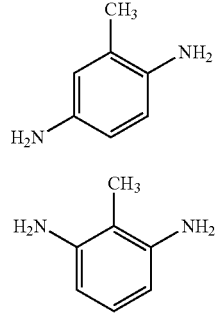
(IVb)
(Vb)

Depending on the isomer or isomers of dinitrotoluene used as starting material, a corresponding isomer or a mixture of at least two isomers of toluenediamine is obtained as product of the process of the invention, i.e. according to the invention, there is preferably no isomerization and/or hydrogenation of the aromatic system during the reaction.

Possible products are therefore selected from among toluene-2,3-diamine (Ib), toluene-3,4-diamine (IIb), toluene-2,4-diamine (IIIb), toluene-2,5-diamine (IVb) and toluene-2,6-diamine (Vb). However, it is also possible according to the invention and preferred for a mixture comprising at least two of the isomers mentioned to be obtained, for example a mixture comprising toluene-2,4-diamine (IIIb) and toluene-2,6-diamine (Vb). Furthermore, it is possible for compounds in which only one nitro group has been hydrogenated to the corresponding amino group and one nitro group has remained in the molecule to be present in the product mixture obtained.

The process is preferably carried out at space-time yields of from 100 to 1000 kg/m$^3$ h, preferably from 150 to 500 kg/m$^3$·h, of aromatic amine. The volume taken into account here is the reactor volume in m$^3$, corresponding to the total volume of the reactor minus the volume of internals present therein.

The process can be carried out either with use of an organic solvent, for example alcohols such as methanol, ethanol, propanol or a mixture thereof, or without addition of an organic solvent.

The process of the invention for preparing aromatic amines by hydrogenation of nitroaromatics by means of hydrogen in the presence of a suspended catalyst in the liquid phase is carried out in a reactor (1),
at one end of which, preferably the upper end, there is a driving jet nozzle (2) via which the reaction mixture taken off from the bottom region of the reactor is injected via an external loop (3) into this region of the reactor (1),
with introduction of the nitroaromatic at one end, preferably the upper end, of the reactor (1) and
introduction of hydrogen, wherein at the correct fill height of the reactor, no direct physical contact between the inlet for the nitroaromatic and the liquid phase, preferably comprising the desired aromatic amine, water and catalyst, can occur in the reactor and/or in the pumped circuit either in the operating state or on shutting down and
partial or complete blocking of the inlet for the nitroaromatic after improper contact between the inlet for the nitroaromatic and the liquid phase in the reactor can be detected by means of measuring instruments.

The process of the invention is preferably carried out in a vertical reactor. The length of the reactor is preferably greater than the width. Suitable dimensions can easily be determined by a person skilled in the art.

The present invention therefore preferably provides the process of the invention in which the reactor (1) is vertical.

The process of the invention is preferably carried out in a reactor in which internal and external loop movement of the reaction mixture takes place.

For this purpose, a preferably vertical reactor is preferably provided at its upper end with a driving jet nozzle which drives the internal loop movement, preferably by the reaction mixture taken off from the bottom region of the reactor being pumped via an external circuit and injected in a downward direction via the driving jet nozzle into the upper region of the reactor.

The reaction mixture injected via the driving jet nozzle preferably flows through a central plug-in tube arranged in the longitudinal direction of the reactor and flows through this from the top downward. The central plug-in tube can be configured as a simple tube. Below the plug-in tube, the direction of movement of the reaction mixture is reversed in an internal loop movement outside the plug-in tube and flows upward again.

The present invention therefore preferably provides the process of the invention in which the reaction mixture which is injected via an external loop (3) subsequently flows into a central plug-in tube (4) which is arranged in the longitudinal direction of the reactor, flows through the length of this, preferably from top downward, and flows upward again in an internal loop movement outside the plug-in tube (4).

To effect flow reversal, an impingement plate is preferably arranged below the plug-in tube.

The loop flow within the reactor, i.e. the internal loop flow, is stabilized by the preferably concentric plug-in tube in combination with the impingement plate which is preferably present.

The driving jet entrains gas from the gas space and introduces it in the form of gas bubbles into the liquid down to the impingement plate. These gas bubbles rise again in the annular space, i.e. between plug-in tube and reactor wall, of the reactor. This internal gas circulation provides a large gas/liquid phase interface.

A heat exchanger through which cooling water flows and takes up part of the heat of reaction is preferably arranged in the interior of the reactor to remove heat.

The present invention therefore preferably provides the process of the invention in which a heat exchanger (6) through which cooling water flows and takes up part of the heat of reaction is present in the interior of the reactor (1).

The heat exchanger arranged in the interior of the reactor is preferably a field tube heat exchanger.

In one embodiment, the heat exchanger arranged in the interior of the reactor is a helical tube heat exchanger.

In a further embodiment, the heat exchanger arranged in the interior of the reactor is a shell-and-tube heat exchanger.

In a further embodiment, the heat exchanger arranged in the interior of the reactor is a plate heat exchanger.

In a preferred embodiment of the process of the invention, a further heat exchanger in addition to the heat exchanger arranged in the interior of the reactor is used in the external loop. This second heat exchanger which is preferably present preferably serves to remove the remaining part of the heat of reaction which cannot be removed via the internal heat exchanger. Preference is given to using a shell-and-tube heat exchanger here.

The present invention therefore preferably provides the process of the invention in which a further heat exchanger (W) in addition to the heat exchanger (6) arranged in the interior of the reactor (1) is used in the external loop.

Steam can be generated from the heat of reaction liberated both in the internal heat exchanger and the external heat exchanger in two ways, firstly by evaporation of part of the cooling water in the cooling tubes (direct steam generation) or by heating the cooling water at a pressure above the pressure of the steam to be generated and subsequently depressurizing the water to the pressure level of the steam to be generated (flash evaporation). In this depressurization, part of the cooling water vaporizes and the steam/water mixture is cooled to the boiling point corresponding to the pressure of the steam.

The two types of vaporization can be employed both in the internal heat exchanger and in the external heat exchanger. A combination of the two types of vaporization is likewise possible, i.e. direct vaporization in the internal heat exchanger and flash evaporation in the external heat exchanger or vice versa.

Depending on, for example, the reaction temperature, the steam generation can also be omitted and the heat can be taken up by recooling water.

Nitroaromatics are preferably fed in at the upper end of the reactor, preferably into the gas phase above the surface of the liquid in the reactor.

In a preferred embodiment of the process of the invention, the introduction of the nitroaromatic is effected via a feed line and/or a metering device.

For the purposes of the invention, it is important to the process of the invention that, at the correct fill height of the reactor, direct physical contact between the inlet for the nitroaromatic and the liquid phase, preferably comprising the desired aromatic amine, water and catalyst, cannot occur in the reactor and/or in the pumped circuit either in the operating state or on shutting down.

For the purposes of the present invention, a correct fill height is a fill height having a liquid surface between the upper edge of a plug-in tube which is preferably present and the outlet opening of the driving jet nozzle. The liquid surface is preferably closer to the outlet opening of the driving jet nozzle than to the upper edge of the plug-in tube.

In a preferred embodiment of the process of the invention, the introduction of the nitroaromatic is effected via a feed line and a metering device without the geometric possibility of dead space formation. Appropriate units or devices are known per se to those skilled in the art. According to the invention, it is essential here that, at the correct fill height of the reactor, direct physical contact between the inlet for the nitroaromatic and the liquid phase, preferably comprising the aromatic amine, i.e. the respective reaction product, water and catalyst, cannot occur in the reactor and/or in the pumped circuit either in the operating state or on shutting down. According to the invention, this is achieved, for example, by the distance between the inlet for the nitroaromatic and the liquid phase being, for example, from 0.01 to 3 m, preferably from 0.05 to 1.0 m.

In a further preferred embodiment of the process of the invention, the introduction of the nitroaromatic is effected via one or more independent pipes in which partial or complete blocking can be detected by means of measuring instruments.

Appropriate pipes are known per se to a person skilled in the art. The pipes which are preferably used are, for example, made of metal, for example black steel or stainless steel. The pipes preferably have diameters determined in accordance with the amounts of nitroaromatics which are fed in.

In general, the pipes which are preferably used can have any suitable cross section.

In a preferred embodiment of the process of the invention, the exit cross section of the inlet for the nitroaromatic has a constriction or a shape deviating from a rotationally symmetric shape at the ends of the one or more independent pipe(s). The outflowing nitroaromatics stream can have laminar or turbulent flow.

It is also advantageous according to the invention for significant local overconcentrations to be avoided when the freshly introduced nitroaromatic is mixed into the reaction mixture. Increased (local) concentrations of nitroaromatics lead to increased by-product formation and deactivation of the suspended catalyst. This results in a loss in yield and thus a higher outlay for product work-up and also increased catalyst costs and capacity reductions. Safety problems can also occur.

A circulating flow is preferably brought about in the interior of the reactor by means of the driving jet of the external circuit. The downward flow region of this circulating flow is determined by the cross-sectional area of the plug-in tube which is preferably present parallel to the reactor axis. The upward flow region is determined by the cross-sectional area of the annular gap between the plug-in tube which is preferably present and the reactor wall.

The driving jet of the external circuit preferably spreads out as a turbulent free jet in the reaction medium. At the perimeter of a turbulent free jet, acceleration and mixing with the surrounding fluid takes place as a result of momentum input.

When nitroaromatics are applied to the surface of the liquid in the interior of the reactor, the effectiveness of mixing-in is accordingly improved with increasing proximity to the region of impingement of the driving jet on the surface of the liquid. The effectiveness of mixing-in determines the spatial extension of the mixing-in zone and also the magnitude of the steady-state nitroaromatics overconcentration occurring therein relative to the total reactor volume.

The present invention therefore preferably provides the process of the invention in which a laminar or turbulent nitroaromatics jet is introduced from one or more of the inlets for the nitroaromatic onto the surface of the liquid phase in the region of the perimeter of the driving jet impinging on the liquid surface from the nozzle of the external circuit.

In the embodiment which is preferred according to the invention in which the reactor used according to the invention has a central plug-in tube (4) which is arranged in the longitudinal direction of the reactor, a laminar or turbulent nitroaromatics jet from one or more of the inlets for the nitroaromatic is, in the process of the invention, introduced onto the surface of the liquid phase in the region of the cross-sectional area of the plug-in tube projected onto the liquid surface, preferably very close to the driving jet from the nozzle of the external circuit, particularly preferably directly at the perimeter of the driving jet of the nozzle of the external circuit.

In a further preferred embodiment of the process of the invention, the exit openings of the one or more inlets for the nitroaromatic are inclined by up to 90° in the direction of the axis of symmetry of the reactor to generate a radial impulse. In this embodiment, the exit openings are inclined by, for example, from 10 to 80°, preferably from 10 to 45°, in the direction of the axis of symmetry of the reactor, i.e. the exit openings of the inlets are preferably inclined in the direction of the middle of the reactor. The nitroaromatics jet therefore does not impinge at right angles onto the liquid phase but at a more acute angle, so that a radial impulse in the direction of the mixing-relevant driving jet results. This contributes to rapid and good mixing being achieved.

Furthermore, the process of the invention has the important feature that partial or complete blocking of the inlet for the nitroaromatic after improper contact between the inlet for the nitroaromatic and the liquid phase in the reactor can be detected by means of measuring instruments.

Measurement methods and devices for detecting such blocking are known per se to those skilled in the art, for example pressure gauges or flow meters. For example, a blockage can be detected by a mass flow decreasing at constant differential pressure. Furthermore, a blockage can, for example, be detected by an increase in the pressure at the appropriate place at a constant mass flow.

The inventors have recognized that it is advantageous to introduce the nitroaromatic, preferably the dinitrotoluene, into the gas phase above the liquid surface in the reactor; this prevents reaction product from flowing back into the feed line for nitroaromatics, preferably dinitrotoluene, and therefore leading to decomposition or explosion of the nitroaromatic. Pure dinitrotoluene, for example, has a decomposition temperature of about 260° C., but the decomposition temperature decreases drastically down to below 100° C. as soon as toluenediamine is mixed in.

It is therefore also advantageous to flush the feed line for the nitroaromatic free with hot water when production is interrupted or the plant is shut down. This applies particularly after a state of incorrect operation, for example overfilling of the reactor.

The inventors have recognized that it is preferable for less than 1000 ppm of nitroaromatic to accumulate in the reactor. For this purpose, it is advantageous to set a nitroaromatics concentration in the range from 1 to 200 ppm in the region between the reactor and the downstream product separation unit. This simultaneously serves as a final control of the mixing and reaction processes in the upstream reactors.

The hydrogen necessary for the hydrogenation is fed in at the lower end of the reactor, preferably via a ring distributor.

A further feature essential to the invention of the process of the invention is that the concentration of hydrogen in the reaction mixture which flows from the bottom region of the reactor into the external loop does not go below 0.1% by volume, preferably 3% by volume. This minimum concentration according to the invention in the reaction mixture ensures, for example, that a desired high conversion of the nitroaromatic, preferably the dinitrotoluene, and thus a low nitroaromatics concentration, preferably dinitrotoluene concentration, are also achieved in the region of the external circulating flow.

In a further preferred embodiment of the process of the invention, additional hydrogen is introduced into the reaction mixture flowing in the external loop, preferably very close to the reactor, in order to ensure the minimum concentration of hydrogen in the external loop.

In a further preferred embodiment of the process of the invention, hydrogen is introduced into the reactor at any position and the reactor diameter or the outflow rate of the reaction mixture from the bottom region of the reactor are designed so that the minimum concentration of hydrogen in the external loop is ensured. The outflow rate of the reaction mixture can be influenced by measures known to those skilled in the art, for example a suitable configuration of the reactor diameter.

To be able to drive an external circuit, a pump which can transport not only liquid but also gas and suspended solid is preferably installed. This should be able to pump up to 20% by volume of gas and up to 20% by weight of suspended solid.

The reaction temperature in the process of the invention is generally from 80 to 200° C., preferably from 100 to 180° C., particularly preferably from 110 to 140° C.

The reaction pressure in the process of the invention is generally from 10 to 50 bar absolute, preferably from 10 to 30 bar absolute, particularly preferably from 20 to 30 bar absolute.

The present invention very particularly preferably provides the process of the invention for preparing toluenediamine (TDA) by hydrogenation of dinitrotoluene (DNT) by means of hydrogen in the presence of a suspended catalyst in the liquid phase in a vertical reactor (1)
at the upper end of which there is a driving jet nozzle (2) via which the reaction mixture taken off from the bottom region of the reactor is injected via an external loop (3) into the upper region of the reactor (1) and subsequently flows into a central plug-in tube (4) arranged in the longitudinal direction of the reactor, flows from the top downward through this and flows upward again in an internal loop movement outside the plug-in tube (4),
having a heat exchanger (6) through which cooling water flows and takes up part of the heat of reaction in the interior of the reactor (1),
with introduction of the DNT at the upper end of the reactor (1) and
introduction of hydrogen at the lower end of the reactor (1),
wherein
at the correct fill height of the reactor, no direct physical contact between the inlet for the DNT and the liquid phase, preferably comprising TDA, water and catalyst, can occur in the reactor and/or in the pumped circuit either in the operating state or on shutting down,
partial or complete blocking of said elements after improper contact between the inlet for the DNT and the liquid phase in the reactor can be detected by means of measuring instruments and
the concentration of hydrogen in the reaction mixture which flows from the bottom region of the reactor into the external loop does not go below 0.1% by volume, preferably 3% by volume.

The present invention also provides an apparatus for carrying out the process of the invention, which comprises at least a reactor (1),
at one end of which, preferably the upper end, there is a driving jet nozzle (2) via which the reaction mixture taken off from the bottom region of the reactor can be injected via an external loop (3) into this region of the reactor (1),
an inlet for the nitroaromatic at one end, preferably the upper end, of the reactor (1),
an inlet for the hydrogen and
a measuring device for determining partial or complete blocking of the inlet for the nitroaromatic after improper contact between the inlet for the nitro aromatic and the liquid phase in the reactor.

The present invention preferably provides the apparatus of the invention in which the reactor is vertical.

Furthermore, the present invention preferably provides the apparatus of the invention in which a central plug-in tube (4) is arranged in the longitudinal direction of the reactor.

Furthermore, the present invention preferably provides the apparatus of the invention in which a heat exchanger (6) through which cooling water flows and takes up part of the heat of reaction is present in the interior of the reactor (1).

Furthermore, the present invention preferably provides the apparatus of the invention in which the hydrogen is introduced at the lower end of the reactor (1).

As regards the individual components and the preferred embodiments of the apparatus of the invention, what has been said above in respect of the process of the invention applies.

FIGURES

FIG. 1A schematically shows a plant for carrying out the process of the invention.

The reactor 1 is equipped in its upper region with a downward-directed driving jet nozzle 2 through which the reaction mixture is injected via an external loop 3 into the reactor. Below the driving jet nozzle 2 there is a central plug-in tube 4 arranged in the longitudinal direction of the reactor and below the plug-in tube 4 there is an impingement plate 5. A field tube heat exchanger 6 is located in the interior of the reactor 1. Dinitrotoluene, DNT, is, in the preferred variant shown in the figure, introduced into the gas space above the liquid surface in the reactor 1 via a single inlet tube 13 which is angled at its end in the direction of the middle of the reactor.

Hydrogen, $H_2$, is injected into the lower region of the reactor 1 via, in the preferred variant shown in the figure, a ring distributor 14 and additionally into the external loop 3 in the vicinity of the offtake for the reaction mixture from the bottom region of the reactor. The reaction mixture is conveyed in the external loop by means of a pump P which is designed so that it can transport up to 20% by volume of gas, in the preferred embodiment shown in the figure via a cross-flow filter 7 serving to discharge the product and a heat exchanger W, which is preferably configured as a shell-and-tube heat exchanger, arranged in the external loop. Steam is taken off via line 8 from the heat exchanger W arranged in the external loop and combined with steam via line 9 from the field tubes which are supplied with water, $H_2O$, fed to a separator 10 and taken off as steam having a gauge pressure of 4 bar via line 11.

FIG. 1B schematically shows a plant for an alternative way of carrying out the process of the invention.

The reactor 1 is equipped in its upper region with a downward-directed driving jet nozzle 2 through which the reaction mixture is injected via an external loop 3 into the reactor. Below the driving jet nozzle 2 there is a central plug-in tube 4 arranged in the longitudinal direction of the reactor and below the plug-in tube 4 there is an impingement plate 5. A field tube heat exchanger 6 cooled by means of secondary cooling water 9 is located in the interior of the reactor 1. Dinitrotoluene, DNT, is, in the preferred variant shown in the figure, introduced into the gas space above the liquid surface in the reactor 1 via a single inlet tube 13 which is angled at its end in the direction of the middle of the reactor.

Hydrogen, $H_2$, is injected into the lower region of the reactor 1 via, in the preferred variant shown in the figure, a ring distributor 14 and additionally into the external loop 3 in the vicinity of the offtake for the reaction mixture from the bottom region of the reactor. The reaction mixture is conveyed via the external loop and two circulation pumps P1 which are connected in series and designed so that they can transport up to 20% by volume of gas and, in the alternative preferred embodiment shown in the figure, back to the driving jet nozzle of the reactor. On the pressure side of the circulation pumps, a substream is taken off via a level regulator and passed to catalyst removal, for example in a gravity separator 12. From this, a catalyst-free or low-catalyst product stream is taken off and a catalyst-enriched suspension is conveyed via a further pump P2 back to the suction side of the circulation pumps.

The further reference numerals in FIGS. 1A and 1B which are not mentioned in the text have the following meanings:
15 Introduction of DNT
16 Introduction of $H_2$
17 Introduction of catalyst
18 Product outlet
19 Steam
20 Water
21 Cooling water
22 Catalyst-enriched suspension

| 15 | Introduction of DNT |
| --- | --- |
| 16 | Introduction of $H_2$ |
| 17 | Introduction of catalyst |
| 18 | Product outlet |
| 19 | Steam |
| 20 | Water |
| 21 | Cooling water |
| 22 | Catalyst-enriched suspension |

Figure 2:
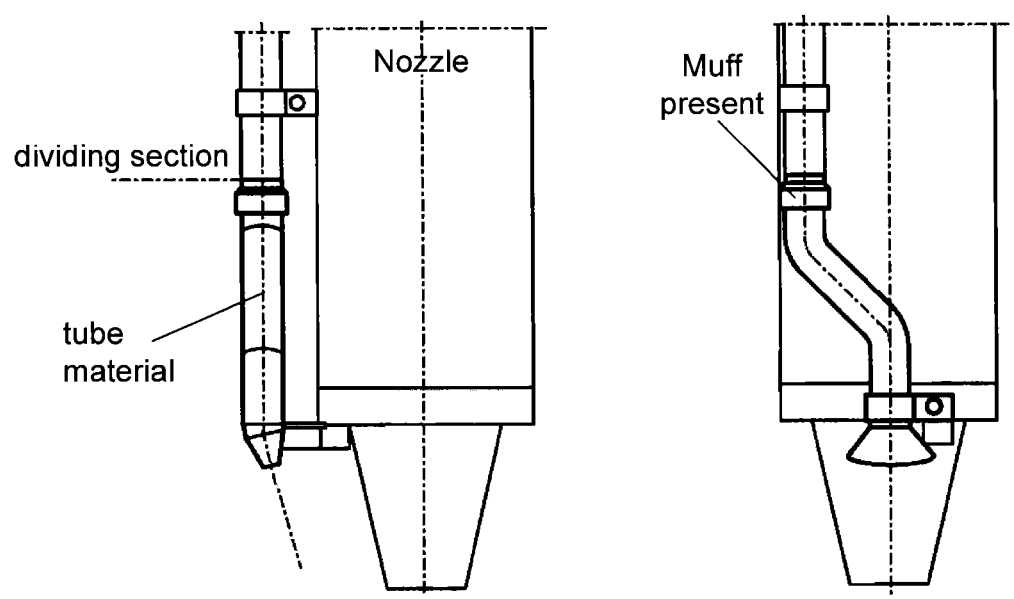

FIG. 2 shows a preferred embodiment of the DNT inlet. This is configured as stainless steel tube whose opening is flattened and angled toward the driving jet nozzle.

EXAMPLES

Example 1

According to the Invention

A cylindrical loop reactor having an external circuit driven by two centrifugal pumps connected in series and opening into a driving jet nozzle arranged centrally at the top of the reactor, a concentric plug-in tube and an impingement plate in the lower part of the reactor to reverse the loop flow (internal circuit) was used. As regards these features, see also WO 2000/35852. The reaction volume of the reactor was about 14 m³. The reactor was provided with a tube bundle composed of parallel field tubes to remove the heat of reaction. The amount of cooling water fed into the field tubes was set so that the temperature in the reactor is maintained at about 120° C. To maintain the loop flow, a volume flow of 580 m³/h was circulated in the external product circuit, resulting in a pressure drop of about 2.3 bar being established over the driving jet nozzle. The reactor comprised about 12 m³ of a liquid hydrogenation bath.

This consisted essentially of a mixture of toluenediamine (TDA) and water in a mass ratio of 0.58:0.42 in which about 4% by weight of a metallic Ni catalyst supported on $SiO_2$ and $ZrO_2$ (produced as described in example 2 of EP 1 161 297 and comminuted by means of a stirred ball mill; here, 10% by volume of the catalyst is made up of particles having a diameter of ≤ about 5 µm, 50% by volume are ≤ about 10 µm and 90% by volume are ≤ about 15 µm, measured by means of laser light scattering (Malvern Mastersizer S) after stirring up in water) were suspended and hydrogen was also dissolved. The liquid surface of the liquid phase was located just below the opening of the driving jet nozzle. Above this, there were about 2 m³ of a gas atmosphere whose hydrogen content was set to from 90 to 95% by volume (in addition to inert gases such as $N_2$) by continuous discharge of a small offgas stream.

7.9 t/h of molten dinitrotoluene (DNT, comprising a mixture of 2,4- and 2,6-DNT isomers in a ratio of about 80:20 and also about 5% of the other DNT isomers and traces of mononitrotoluene) maintained at about 80° C. were injected by means of a membrane piston metering pump into the gas space of the reactor. The introduction into the reactor was effected via the angled stainless steel tube shown in FIG. 2 whose opening was flattened and angled at an angle of 13° toward the driving jet nozzle. The volume flow through the line and the pressure drop over the line were monitored continuously.

A pressure of 25 bar gauge was set in the reactor by simultaneous introduction of about 0.54 t/h of hydrogen (diluted with about 2 kg/h of $N_2$). 95% of the hydrogen was introduced via a nozzle ring above the impingement plate and 5% at the reactor outlet, in each case into the hydrogenation bath. The reaction proceeded under largely isothermal conditions: the reaction temperature was within the range from 117 and 127° C. over the entire reactor. In addition, 625 kg/h of a suspension of the abovementioned catalyst in water (partly separated off from the hydrogenation product in the work-up section) were introduced, likewise continuously, by means of a diaphragm pump. The amount of catalyst comprised in this suspension was varied in a targeted manner in the range from 0 to 5 kg/h to set the DNT concentration and was on average about 1.4 kg/h.

To keep the liquid level in the reactor constant, an appropriate amount of hydrogenation product was taken off continuously from the external product circuit on the pressure side of the 2nd centrifugal pump and introduced into a lamella clarifier having a liquid volume of about 50 m³ and a gas volume of about 10 m³. The catalyst was able to concentrate in the lower region of this. 18 m³/h of an appropriately thickened suspension were then recirculated to the suction side of the 1st centrifugal pump. At the same time, about 9.1 t/h of hydrogenation product were taken off from the lamella clarifier via an overflow. This comprised about 5.2 t/h of TDA (having an isomer distribution corresponding to that of the DNT used), about 0.1 t/h of low and high boilers (in a ratio of about 20:80) and about 3.8 t/h of water and up to about 1 kg/h of catalyst (mostly fines). The hydrogenation product went, like the hydrogenation products from other reactors, via a pressure reduction into a common intermediate vessel and was from this fed continuously to the work-up by distillation. The parts in contact with product were partly made of black steel (St37) and partly of stainless steel (1.4571).

To determine the content of DNT and aminonitrotoluenes (partially hydrogenated intermediates) in the hydrogenation bath, samples of suspension were taken from the line from the external product circuit of the loop reactor to the lamella clarifier at intervals of not more than 4 hours. These were freed of the suspended solid by filtration and the concentration of the nitro compounds comprised therein was determined by means of polarography. The DNT concentration was set in the range from 3 to 30 ppm (average: 10 ppm) and the aminonitrotoluene concentration was set in the range from 1 to 200 ppm (average: 3 ppm) by adapting the catalyst concentration in the aqueous suspension (see above) fed to the reactor.

The reactor was operated under the abovementioned conditions for 2 months without appreciable interruptions. During this time, the crystallite size determined by means of X-ray powder diffraction of the Ni catalyst filtered off from the above samples of suspension increased from 10 nm to 13 nm as a result of sintering.

Before and after the introduction of a DNT, the DNT line was flushed with about 50 l of deionized water in the direction of the reactor.

Blocking of the nozzle was not detected either during this continuous operation or at any other point in time (e.g. during charging and emptying steps). No blockages or deposits could be observed during a routine inspection either.

Comparative Example 1

The reaction was carried out as described in example 1, likewise for 2 months. However, a DNT ring distributor having six openings directed essentially vertically downward was used instead of the DNT single-tube nozzle described in example 1. Here, only 7.5 t/h of DNT could be reacted at comparable DNT and ANT concentrations and a comparable amount of introduced catalyst. Accordingly, about 0.50 t/h of hydrogen was fed in. Despite this reduced amount of DNT to be reacted, the amount of catalyst comprised in the aqueous suspension introduced had to be set to an average of about 1.6 kg/h to set the DNT concentration (average: 11 ppm) and aminonitrotoluene concentration (average: 1 ppm) in the ranges indicated in example 1. About 8.6 t/h of hydrogenation product were taken off. This comprised about 4.9 t/h of TDA (with an isomer distribution corresponding to that of the DNT used), about 0.1 t/h of low and high boilers (in a ratio of about 20:80) and about 3.6 t/h of water and up to about 1 kg/h of catalyst (mostly fines).

During the 2-month reaction, the crystallite size determined by means of X-ray powder diffraction of the Ni catalyst filtered off from the above samples of suspension increased from 10 nm to 14 nm as a result of sintering.

The DNT line was in this case, too, flushed with about 50 l of deionized water in the direction of the reactor.

Blocking of the DNT ring distributor could likewise not be detected either during this continuous operation or at any other point in time (e.g. during charging and emptying steps). However, the routine inspection revealed a blockage comprising polymer, TDA, catalyst and DNT in the part of the DNT ring distributor furthest from the feed line.

The invention claimed is:

1. A process for preparing an aromatic amine, the process comprising:
    hydrogenating a nitroaromatic with hydrogen in the presence of a suspended catalyst in a liquid phase and in a reactor, thereby obtaining the aromatic amine,
    wherein at one end of the reactor is a driving jet nozzle via which a reaction mixture from a bottom region of the reactor is injected via an external loop into the one end of the reactor,
    the process comprises introducing the nitroaromatic at the one end of the reactor with an inlet that is distinct from the driving jet nozzle,
    the process further comprises introducing hydrogen,
    at a correct fill height of the reactor, direct physical contact between the inlet for the nitroaromatic and the liquid phase occurs neither in the reactor nor in a pumped circuit, either in an operating state or on shutting down, and
    a measuring instrument is configured to detect partial or complete blocking of the inlet for the nitroaromatic after improper contact between the inlet for the nitroaromatic and the liquid phase in the reactor.

2. The process according to claim 1, wherein the reactor is vertical.

3. The process according to claim 1, wherein the reaction mixture which is injected via an external loop:
    subsequently flows into a central plug-in tube which is arranged in a longitudinal direction of the reactor,
    flows through the length of the central plug-in tube, and
    flows upward again in an internal loop movement outside the plug-in tube.

4. The process according to claim 3, comprising introducing a laminar or turbulent nitroaromatics jet from an inlet for the nitroaromatic onto a surface of the liquid phase in a region of a cross-sectional area of the plug-in tube projected onto the liquid surface.

5. The process according to claim 1, wherein a heat exchanger is present in an interior of the reactor and is configured to allow cooling water to flow and take up part of the heat of reaction.

6. The process according to claim 5, wherein the external loop comprises a further heat exchanger in addition to the heat exchanger in the interior of the reactor.

7. The process according to claim 1, wherein the hydrogen is introduced at a lower end of the reactor.

8. The process according to claim 1, wherein a concentration of hydrogen in the reaction mixture which flows from the bottom region of the reactor into the external loop is not below 0.1% by volume.

9. The process according to claim 8, further comprising introducing hydrogen into the reactor at any place,
    wherein a reactor diameter or an outflow rate of the reaction mixture from the bottom region of the reactor is configured to ensure a minimum concentration of hydrogen in the external loop.

10. The process according to claim 1, wherein the introducing the nitroaromatic is with a feed line, a metering device, or any combination thereof.

11. The process according to claim 10, wherein the introducing the nitroaromatic is with an independent pipe configured to detect partial or complete blocking with a measuring instrument.

12. The process according to claim 11, wherein an exit cross section of the inlet for the nitroaromatic has a constriction or a shape deviating from a rotationally symmetric shape at ends of the independent pipe.

13. The process according to claim 1, comprising introducing a laminar or turbulent nitroaromatics jet from an inlet for the nitroaromatic onto a surface of the liquid phase in a region of a perimeter of the driving jet impinging on the liquid surface from the nozzle of the external loop.

14. The process according to claim 1, wherein an outlet opening of inlets for the nitroaromatic are inclined by up to 90° in a direction of an axis of symmetry of the reactor, thereby generating a radial impulse.

15. The process according to claim 1, further comprising introducing additional hydrogen into the reaction mixture flowing in the external loop, thereby ensuring a minimum concentration of hydrogen in the external loop.

16. The process according to claim 1, wherein the reaction temperature is from 80 to 200° C.

17. The process according to claim 1, wherein the reaction pressure is from 10 to 50 bar absolute.

* * * * *